(12) United States Patent
Duncan et al.

(10) Patent No.: US 9,410,903 B2
(45) Date of Patent: Aug. 9, 2016

(54) INCOHERENT REFLECTOMETRY UTILIZING CHAOTIC EXCITATION OF LIGHT SOURCES

(75) Inventors: Roger Glen Duncan, Christiansburg, VA (US); Brooks A. Childers, Christiansburg, VA (US); Philip Robin Couch, Devon (GB)

(73) Assignee: BAKER HUGHES INCORPORATED, Houston, TX (US)

( * ) Notice: Subject to any disclaimer, the term of this patent is extended or adjusted under 35 U.S.C. 154(b) by 1202 days.

(21) Appl. No.: 13/271,968

(22) Filed: Oct. 12, 2011

(65) Prior Publication Data

US 2013/0093599 A1 Apr. 18, 2013

(51) Int. Cl.
*G01V 3/00* (2006.01)
*G01N 21/954* (2006.01)

(52) U.S. Cl.
CPC .................... *G01N 21/954* (2013.01)

(58) Field of Classification Search
CPC .. G01N 21/00; G01N 21/954; G01D 5/35383
USPC ................ 340/850–856; 385/12; 398/78, 87; 356/73.1
See application file for complete search history.

(56) References Cited

U.S. PATENT DOCUMENTS

| | | | |
|---|---|---|---|
| 5,513,196 A * | 4/1996 | Bischel et al. ............. | 372/22 |
| 5,579,328 A * | 11/1996 | Habel et al. ............... | 372/31 |
| 5,675,674 A * | 10/1997 | Weis ......................... | 385/12 |
| 6,285,806 B1 * | 9/2001 | Kersey et al. ............. | 385/12 |
| 6,892,031 B2 * | 5/2005 | Lee .......................... | 398/78 |
| 7,453,100 B2 | 11/2008 | Funabashi et al. | |
| 7,548,319 B2 * | 6/2009 | Hartog ..................... | 356/478 |
| 2004/0027560 A1 * | 2/2004 | Fredin et al. ............. | 356/73.1 |
| 2004/0091009 A1 * | 5/2004 | Matsuda et al. .......... | 372/43 |
| 2006/0072638 A1 * | 4/2006 | Tanaka ..................... | 372/38.02 |
| 2007/0098032 A1 * | 5/2007 | Johnson ................... | 372/50.11 |
| 2007/0131418 A1 * | 6/2007 | Barrow et al. ............ | 166/255.1 |
| 2008/0095203 A1 * | 4/2008 | Bratkovski et al. ....... | 372/26 |
| 2010/0092176 A1 * | 4/2010 | Hartog et al. ............. | 398/79 |
| 2011/0142085 A1 * | 6/2011 | Yousefi .................... | 372/20 |
| 2011/0217036 A1 * | 9/2011 | Campanelli et al. ...... | 398/13 |
| 2011/0228255 A1 * | 9/2011 | Li et al. .................... | 356/33 |

OTHER PUBLICATIONS

Ryu, et al. "Incoherent Optical Frequency Domain Reflectometry for Health Monitoring of avionics Fiber Optics Networks" . IEEE, Avionics, Fiber-Optics and Photonics Technology conference. Sep. 30-Oct. 2, 2008. pp. 15-16.

* cited by examiner

*Primary Examiner* — Hai Phan
*Assistant Examiner* — Royit Yu
(74) *Attorney, Agent, or Firm* — Cantor Colburn LLP

(57) ABSTRACT

A method for estimating a parameter includes: transmitting a control signal to a coherent optical source, the control signal configured to chaotically vary an output of the optical source and generate a chaotically excited optical signal; transmitting the optical signal from the optical source into an optical fiber, the optical fiber including at least one sensing location; receiving a reflected signal including light reflected from the at least one sensing location; and estimating a value of the parameter using the reflected signal.

14 Claims, 4 Drawing Sheets

INCOHERENT REFLECTOMETRY UTILIZING CHAOTIC EXCITATION OF LIGHT SOURCES

BACKGROUND

Parameter monitoring systems can be incorporated with downhole components as fiber-optic distributed sensing systems (DSS). Examples of DSS techniques include Optical Frequency Domain Reflectometry (OFDR), which includes interrogating an optical fiber sensor with an optical signal to generate reflected signals scattered from sensing locations (e.g., fiber Bragg gratings) in the optical fiber sensor.

Some monitoring systems utilize incoherent reflectometry techniques, such as frequency modulated incoherent reflectometry and incoherent OFDR, which involve interrogating an optical fiber sensor with a modulated optical signal and combining return signals with modulated reference signals in the electric domain. Coherent light sources such as lasers are used to produce coherent optical signals, and many of the qualities of coherent sources are desirable. However, under some conditions, coherence can produce some undesirable effects in such techniques.

SUMMARY

A method for estimating a parameter includes: transmitting a control signal to a coherent optical source, the control signal configured to chaotically vary an output of the optical source and generate a chaotically excited optical signal; transmitting the optical signal from the optical source into an optical fiber, the optical fiber including at least one sensing location; receiving a reflected signal including light reflected from the at least one sensing location; and estimating a value of the parameter using the reflected signal.

A system for estimating a parameter includes: a coherent optical source in optical communication with an optical fiber, the optical source configured to generate an optical signal, the optical fiber configured to receive the optical signal and including a plurality of sensing locations disposed along the optical fiber and configured to reflect light; a controller in communication with the optical source, the controller configured to transmit a control signal to the optical source, the control signal configured to chaotically vary an output of the optical source and generate a chaotically excited optical signal; a detector configured to receive a reflected signal including light reflected from the at least one sensing location; and a processor configured to estimate a value of the parameter using the reflected signal.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings, wherein like elements are numbered alike, in which:

DETAILED DESCRIPTION

There are provided systems and methods for interrogating one or more optical fibers. A method includes generating an optical signal from a coherent light source and launching the optical signal into an optical fiber including one or more sensing location disposed along a length of the optical fiber. In one embodiment, the optical signal is modulated using an oscillating modulation signal having a time-varying oscillation frequency (i.e., modulation frequency). A control signal is generated to chaotically excite the light source to reduce the coherence of the optical signal. For example, a chaotic signal is generated to excite an optical signal having a substantially constant wavelength and a chaotically or randomly varying phase and thus a reduced temporal coherence. In another example, a modulated optical signal is generated that has a randomly or chaotically varying wavelength. The systems and methods provided herein include chaotic excitation of coherent light sources to reduce the coherence of optical signals produced by the light sources in order to moderate some deleterious effects produced by coherence between interrogation signals, launch reflection signals and/or sensing location reflection signals.

Figure 1:
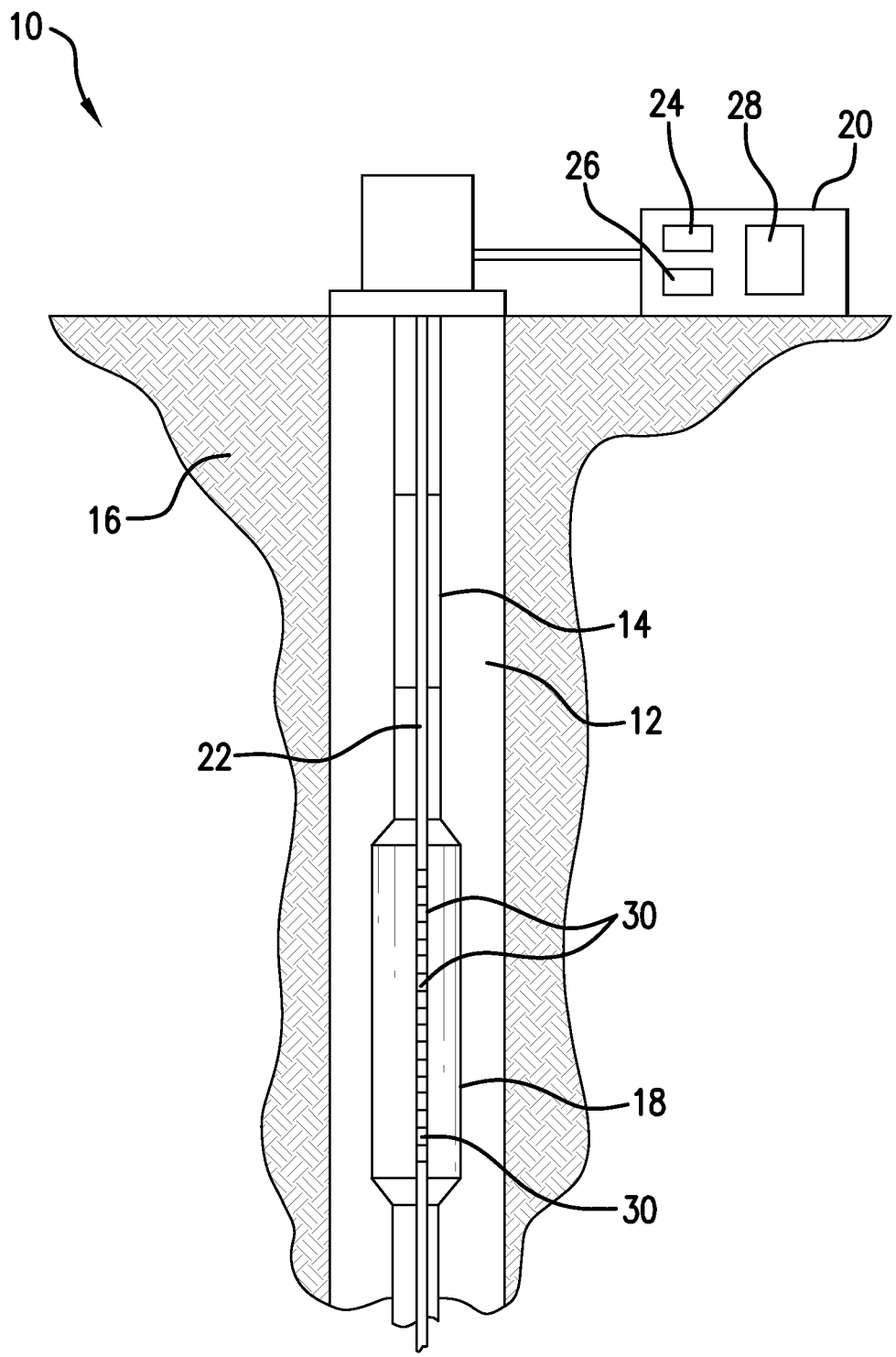
FIG. 1 illustrates an exemplary embodiment of a downhole drilling, monitoring, evaluation, exploration and/or production system.

Referring to FIG. 1, an exemplary embodiment of a downhole drilling, monitoring, evaluation, exploration and/or production system 10 disposed in a wellbore 12 in an earth formation 16 is shown. A borehole string 14 is disposed in the wellbore 12 and performs or facilitates functions such as drilling, production and formation evaluation. The borehole string 14 is made from, for example, a pipe, multiple pipe sections or flexible tubing. The borehole string 14 includes for example, a drilling system and/or a bottomhole assembly (BHA). The system 10 and/or the borehole string 14 include any number of downhole tools 18 for various processes including drilling, hydrocarbon production, and formation evaluation (FE) for measuring one or more physical quantities in or around a borehole. Various measurement tools 18 may be incorporated into the system 10 to affect measurement regimes such as wireline measurement applications or logging-while-drilling (LWD) applications.

In one embodiment, a parameter measurement system is included as part of the system 10 and is configured to measure or estimate various downhole parameters of the formation 16, the borehole 14, the tool 18 and/or other downhole components. The measurement system includes an optical interrogator or measurement unit 20 connected in operable communication with at least one optical fiber 22. The measurement unit 20 may be located, for example, at a surface location, or may be incorporated with the borehole string 12 or tool 18 or otherwise disposed downhole as desired. The measurement unit 20 includes, for example, an electromagnetic signal source 24 such as a tunable light source, a LED and/or a laser, and a signal detector 26. In one embodiment, a processor 28 is in operable communication with the signal source 24 and the detector 26 and is configured to control the source 24, receive reflected signal data from the detector 26 and/or process reflected signal data. Although the measurement unit 20 is shown as a single unit, it can also be configured as multiple units. Furthermore, the measurement system described herein is not limited to downhole applications. The measurement system may be used in conjunction with any surface or downhole environment, particularly those that would benefit from distributed parameter (e.g., temperature or pressure) measurements.

The optical fiber 22 is operably connected to the measurement unit 20 and is configured to be disposed downhole. The optical fiber 22 includes one or more sensing locations 30 disposed along a length of the optical fiber. The sensing locations 30 are configured to reflect and/or scatter optical interrogation signals transmitted by the measurement unit 20. Examples of sensing locations include fiber Bragg gratings (FBG), mirrors, Fabry-Perot cavities and locations of intrinsic scattering. Locations of intrinsic scattering include points in or lengths of the fiber that reflect interrogation signals, such as Rayleigh scattering, Brillouin scattering and Raman scattering locations. The sensing locations 30 are configured to return reflected and/or backscattered signals, referred to herein collectively as "reflected signals" or "return signals," from the sensing locations 30 in response to optical measurement signals (i.e., interrogation signals) launched into the optical fiber 22. Reflected or return signals may also include any signals resulting from reflection of interrogation signals, including reflections from an optical coupling or any other features of the optical fiber that cause reflection.

In one embodiment, the measurement system is configured as an incoherent reflectometry system, such as an incoherent optical frequency-domain reflectometry (IOFDR) system. In IOFDR, the interrogation signal is frequency modulated over time (e.g., periodically) via a modulation signal (see, for example, FIG. 4). The frequency may be modulated in a step-wise manner or continuously (swept frequency). The interrogation signal is transmitted into the optical fiber and reflected signals are returned from the sensing locations and detected as a function of modulation frequency. In one embodiment, the reflected signals are mixed with the original modulation signal or another modulation signal in the electrical domain (referred to as a "reference signal"), to generate a distance encoded signal. A Fourier transformation (e.g., Fast Fourier Transform) of the interference signal as a function of frequency provides the time-domain signal, which can be used to correlate the interference signal with locations along the fiber. A Fourier transform (e.g., Fast Fourier Transform) of the distance encoded signal allows reflected signals to be correlated with locations along the fiber.

Figure 2:
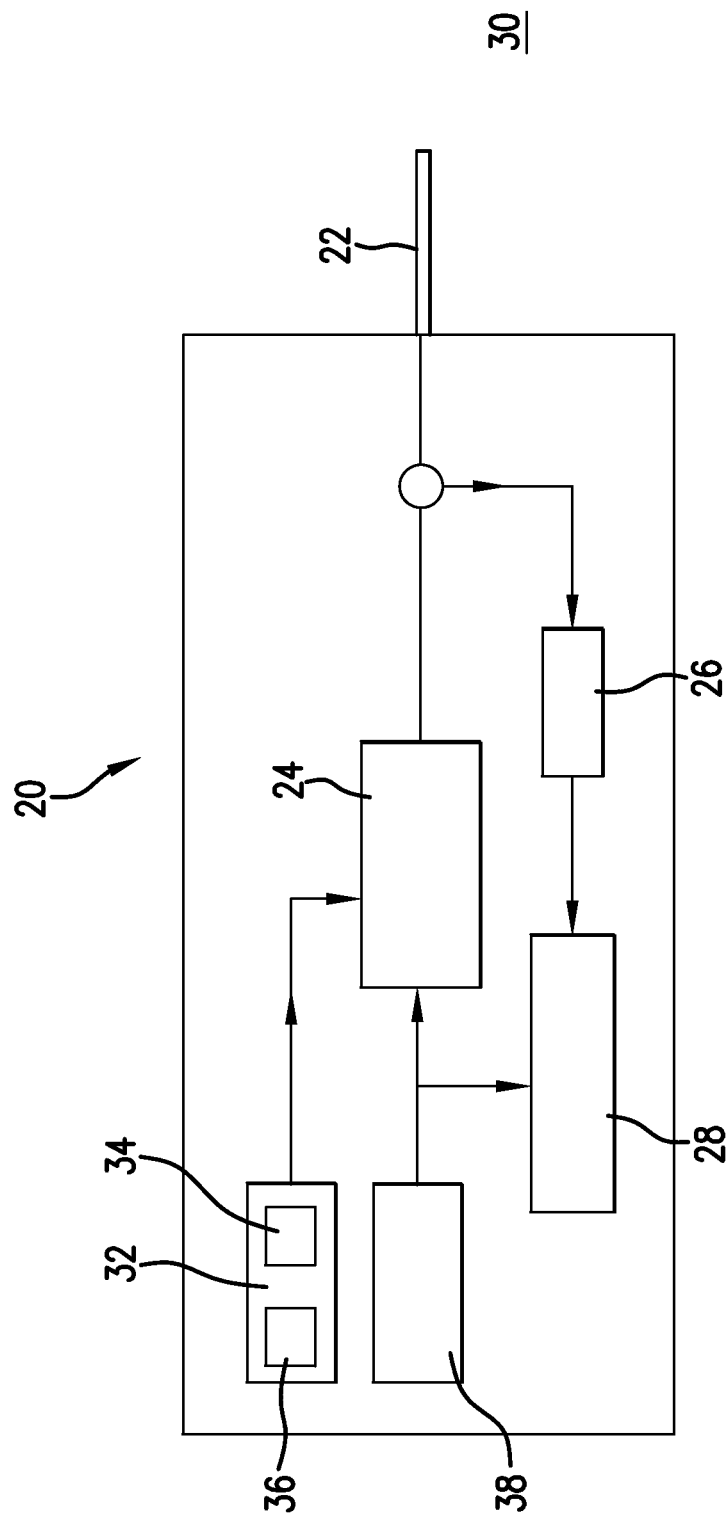
FIG. 2 illustrates an exemplary embodiment of a measurement unit of the system of FIG. 1.

An example of the measurement unit 20 is shown in FIG. 2. In this example, the measurement unit is an incoherent OFDR device. The measurement unit 20 includes the optical source 24, such as a continuous wave (cw) frequency (or wavelength) tunable diode laser optically connected to the optical fiber 22. A detector 26, such as a photodiode, is included to detect reflected signals from the optical fiber 22 in response to modulated optical signals launched from the optical source 24.

An optical source controller 32 is included in the measurement unit 20 to control excitation and/or modulation of the optical source 24. The controller 32 is configured to chaotically or randomly excite the optical source 24. For example, the controller is configured to inject a chaotic signal that chaotically or randomly varies the phase of the optical source output over time. The chaotic signal may also be used to chaotically or randomly vary the amplitude. Chaotic excitation produces an optical signal having a reduced temporal coherence relative to a steady driving current or a driving current that is modulated with a constant or controllable modulation frequency. Such excitation increases the phase noise of the source, reducing the coherence of the optical source and reducing the deleterious effects of coherence noise that can be experienced during incoherent reflectometry operations. Examples of chaotic generators include random number generators, pseudo-random number generators and noise generators. These signal generators are applied to an input of the optical source 24 to create a chaotically varying optical signal.

In one embodiment, the optical source 24 is an electrically driven source such as a distributed feedback (DFB) laser, and the controller 32 includes a driving current source 34 configured to deliver a current (I) to the laser and excite an optical signal having a corresponding power. In one embodiment, the controller 32 includes a current modulator 36 configured to introduce a modulation signal to the input current. For example, an oscillation function generator such as a sine wave or square wave generator is used to modulate the current. The current modulation frequency may be chaotically or randomly modified over time via the current modulator 36, which introduces noise into the current and correspondingly decreases the coherence (e.g., coherence length) of the optical signal generated by the laser. The current modulation frequency may be chaotically modified via any suitable mechanism, such as a white noise generator or a random number generator. For example, as shown in FIG. 2, the controller 32 injects a chaotic or random signal into the modulator 36 to chaotically or randomly vary the phase and/or amplitude of the optical signal.

As described herein, "chaos" or "chaotic excitation" refers to applying some random, pseudo-random or non-continuous changes to an excitation source, such as an electrical source as described herein or an optical signal. Chaotic, in some embodiments, refers to modulation according to a deterministic, though complex, system. In other embodiments, chaotic refers to a true random or pseudo-random excitation.

The measurement unit 20 includes an optical signal modulator (e.g., function generator) 38 in optical communication with the tunable optical source 24. The signal modulator 38 is configured to modulate the optical source 24 by power, intensity or amplitude, using a modulation signal. The modulation signal is generally an oscillating waveform, such as a sine wave, having an oscillation or modulation frequency. In one embodiment, the signal modulator 38 may be incorporated as part of the optical source 24. In one embodiment, each of the modulation signal and the reference signal are oscillating signals having a time-varying oscillation frequency, also referred to as the "modulation frequency". Each modulation signal includes a respective oscillation frequency or modulation frequency that varies over time according to some function, such as a step function or a linear function.

The optical source 24 may be a tunable laser such as DFB, diode laser or dye laser. In one embodiment, the controller 32 is configured to chaotically or randomly modulate the wavelength of the optical signal that is launched into the measurement system. For example, the optical signal is generated having a substantially constant central wavelength. The wavelength is rapidly modulated by a small magnitude (e.g., around 0.01 nanometers) that differs rapidly over time according to a random or chaotic function. For example, the wavelength can be periodically changed by a random amount within a selected linewidth over a selected time period. The time period can be selected based on, e.g., signal transit time, so that each wavelength change can be correlated with a selected location. The number of wavelength changes may be modified as needed to correspond to any number of locations. Because of the random or chaotic change, the instantaneous evolution of the wavelength can be monitored and recorded for reflections from one or more reflectors, including the sensing locations 30. Each wavelength can be correlated with a reflector at some given distance into the fiber. The pattern of wavelength changes can be repeated, allowing the wavelength of subsequent return signals at any point in time to be predicted. Thus, the return signal can be analyzed according to wavelength and modulation frequency. For example, each digitized sample of return signal could be put into a bin for that respective wavelength. After sweeping modulation for some time, one could build up a picture spanning both modulation frequencies and wavelengths.

Although chaotic excitation and/or chaotic wavelength modulation is described as being performed by the controller 32, the systems and methods described herein are not so limited. For example, chaotic excitation and/or modulation may be performed by any processor or combination of processors and signal sources, such as the modulator 38, the processor 28 or some other downhole or surface device.

Still referring to FIG. 2, a computer processor 28 is coupled to at least the detector 26, and is configured to process the reflected light signals. For example, the computer processing system 28 can demodulate the reflected signal using a reference power, intensity and/or amplitude modulation signal, such as the modulation signal generated by the modulator 38 or another local oscillator. The processor 28 can be configured as or can include a network analyzer, which measures the amplitude and phase of the modulation signal or reference signal with respect to the received reflected signal. The processing system 28 may also be configured to further process the demodulated signal. For example, the processor 28 is configured to transform (e.g., via a FFT) the reflected signal to allow spatial correlation of the signal with the sensing locations 30 or selected locations or regions of the optical fiber 22. In another example, for a return signal whose wavelength has been chaotically modulated, the processor 28 can analyze the return signal according to both modulation frequency and wavelength. Various additional components may also be included as part of the measurement unit 20, such as a spectrum analyzer, beam splitter, light circulator, gain meter, phase meter, lens, filter and fiber optic coupler for example.

Figure 3:
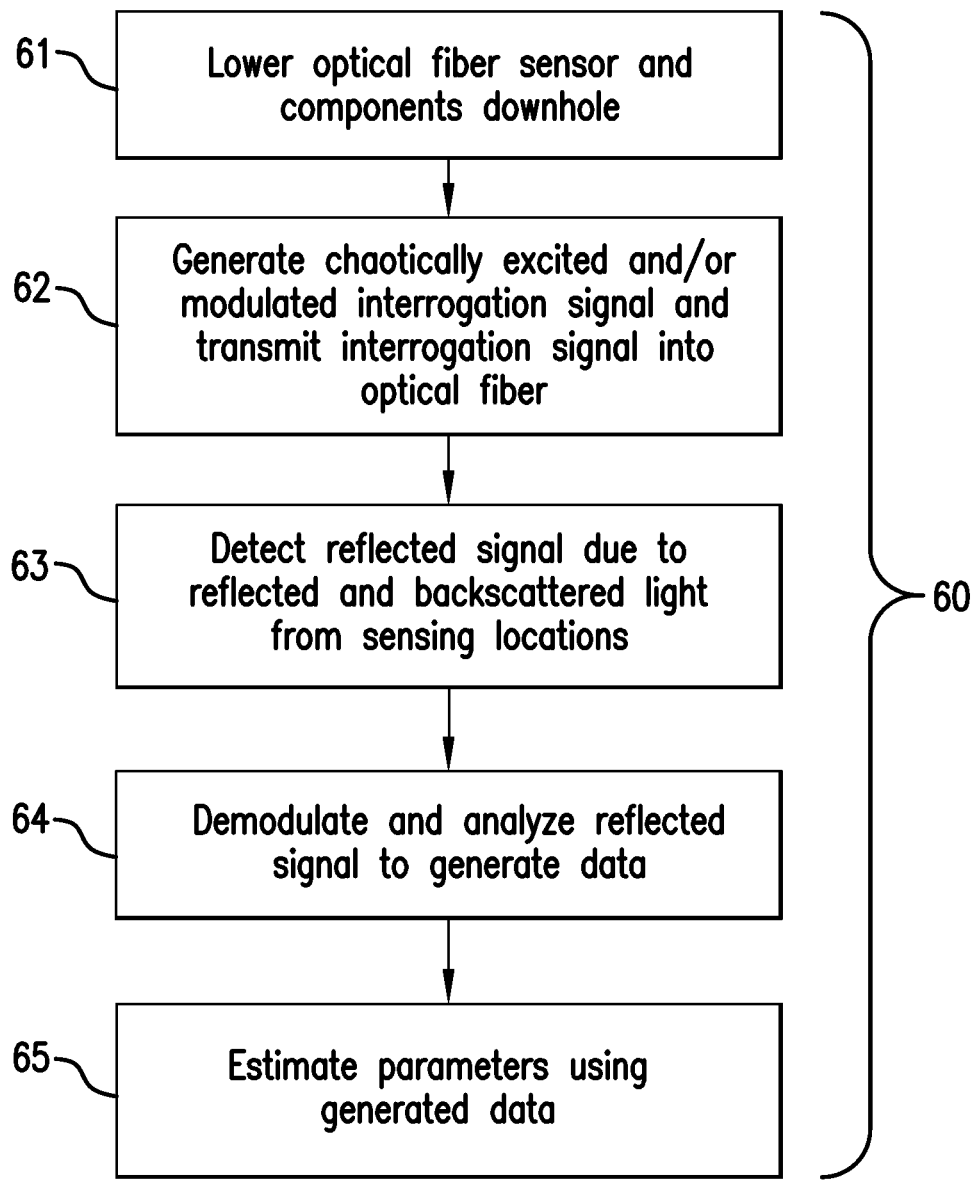
FIG. 3 is a flow chart illustrating an exemplary embodiment of a method of estimating a parameter.

FIG. 3 illustrates a method 60 of measuring downhole parameters. The method 60 includes one or more stages 61-65. Although the method 60 is described in conjunction with the system 10 and the measurement systems described above, the method 60 is not limited to use with these embodiments, and may be performed by the measurement unit 20 or other processing and/or signal detection device. In one embodiment, the method 60 includes the execution of all of stages 61-65 in the order described. However, certain stages may be omitted, stages may be added, or the order of the stages changed.

In the first stage 61, the optical fiber 22 along with the borehole string 12, tools 18 and/or other components are lowered downhole. The components may be lowered via, for example, a wireline or a drillstring.

In the second stage 62, a modulated optical signal having a wavelength is generated. The optical signal is modulated or excited according to a chaotic or random modulation or excitation, and launched into the optical fiber.

In one embodiment, the optical source (e.g., laser) is chaotically excited by inputting a source of noise into the optical source. For example, a driving current is input to a laser, and the controller modulates the driving current using a chaotically or randomly changing signal. The resulting optical signal, having a coherence reduced by the chaotic excitation, is further modulated by power, intensity and/or amplitude.

The optical signal is modulated by amplitude, power or intensity (e.g., using a modulation signal from the modulator 38) according to a sinusoidal or other oscillating function having a time-varying oscillation frequency or modulation frequency. In general, the modulation frequencies are in the radio frequency range, although other frequencies can be used down to zero Hertz.

Figure 4:
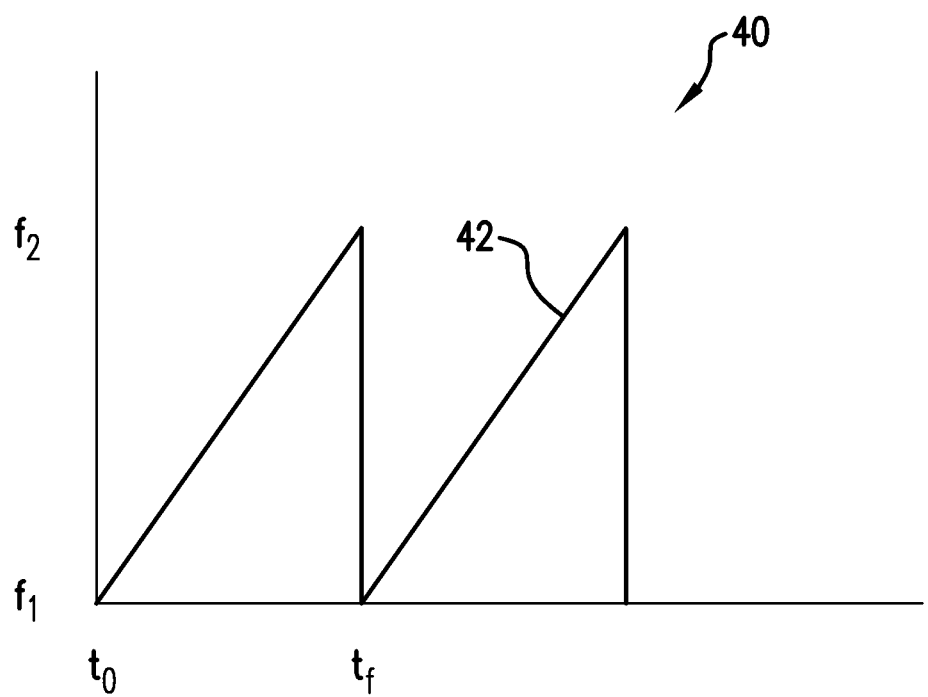
FIG. 4 is an illustration of a modulation frequency of a modulated optical signal.

For example, as shown in FIG. 4, the modulation frequency varies over time according to a selected function. For example, the optical signal modulation frequency is swept, i.e., changed, by the modulator 38 over a period of time, such as in a continuous or nearly continuous change (e.g., linear change, exponential). For example, the modulator 38 modulates the optical signal with a modulation signal 40 having a modulation frequency represented by a linear function 42. In this example, the function begins at an initial time "$t_0$", at which the modulation frequency is at a selected minimum "$f_1$" (e.g., at or near zero), and ends at a time "$t_f$", at which the modulation frequency is a selected maximum "$f_2$". The function may repeat as desired. Multiple modulated signals may be iteratively launched for multiple laser wavelengths.

In one embodiment, the optical source is chaotically or randomly excited by modulating the wavelength of the optical signal according to a randomly or chaotically varying function. For example, the wavelength is chaotically or randomly changed around the selected central wavelength.

In the third stage 63, a reflected signal is detected by the detector 26 and corresponding return or reflected signal data is generated by the processor 28. The reflected signals may include light reflected and/or backscattered from sensing locations 30. For example, the reflected signal is a result of reflections and/or backscattering from features such as mirrors, point defects, network elements, bends, FBGs, Rayleigh scattering, Raman scattering, Brillouin scattering and others.

In the fourth stage 64, the reflected signal is analyzed to generate data indicative of parameters (e.g., temperature and pressure) along the optical fiber.

In one embodiment, the reflected signal is mixed or demodulated with respect to a reference signal, such as the modulation signal. For example, the reference signal has an oscillating form, e.g., is a sinusoidal waveform having a modulation frequency that is varied over time.

The demodulated reflected signals may then be transformed using a mathematical algorithm such as a Fast Fourier Transform (FFT) into the time domain.

In one embodiment, for a return signal that has been received in response to an optical signal that has been wavelength modulated, the instantaneous wavelength of the return signal is analyzed. For example, the return signal is analyzed to correlate portions of the return signal to locations of reflectors in the optical fiber. Furthermore, the return signal may be analyzed according to wavelength and modulation frequency, for example, by binning samples of the return signal by wavelength.

Stages 61-64 may be repeated for optical signals having multiple optical wavelengths. For example, stages 61-64 are performed using a modulated signal having a first substantially constant first wavelength $\lambda_1$ (or a substantially constant central wavelength), and repeated for N subsequent signals having wavelengths $\lambda_2$-$\lambda_N$. Multiple sets of readings may be assembled into one composite set of readings, which provides a complex data set containing, among other parameters, amplitude of reflection (or transmission) and spatial location data for each of the components in optical communication with the optical fiber 22. The stages may also be performed using a swept or continuous wavelength change. The methods described herein are not limited to IOFDR. For example, the methods may also be used for optical time domain reflectometry (OTDR).

In the fifth stage 65, the analyzed signal data is utilized to estimate various parameters along the optical fiber 22. The reflected signal data is correlated to locations on or lengths of the optical fiber 22, and parameters are estimated for one or more sensing locations 30. Examples of such parameters include temperature, pressure, vibration, force, strain and deformation of downhole components, chemical composition of downhole fluids or the formation, acoustic events, and others.

The systems and methods described herein provide various advantages over prior art techniques. The systems and methods provide a mechanism for reducing the effects coherence between various light signals reflected from the optical fiber, as well as coherence between the launched optical signal and return signals.

In support of the teachings herein, various analysis components may be used, including a digital and/or an analog system. Components of the system, such as the measurement unit 20, the processor 28 and other components of the system 10, may have components such as a processor, storage media, memory, input, output, communications link, user interfaces, software programs, signal processors (digital or analog) and other such components (such as resistors, capacitors, inductors and others) to provide for operation and analyses of the apparatus and methods disclosed herein in any of several manners well appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

It will be recognized that the various components or technologies may provide certain necessary or beneficial functionality or features. Accordingly, these functions and features as may be needed in support of the appended claims and variations thereof are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for estimating a parameter, the method comprising:

transmitting a control signal to a coherent optical source, the coherent optical source configured to emit an optical signal having a central wavelength, the control signal configured to chaotically vary a wavelength of the optical source and generate a chaotically excited optical signal, wherein chaotically varying the wavelength introduces noise and decreases the coherence of the optical signal, and chaotically varying the wavelength includes periodically applying a random wavelength change relative to the central wavelength, each wavelength change correlated with a different sensing location;

modulating the optical signal via an oscillating modulation signal having a time-varying modulation frequency;

transmitting the optical signal from the optical source into an optical fiber, the optical fiber including at least one sensing location;

receiving a reflected signal including light reflected from the at least one sensing location; and determining the modulation frequency and an instantaneous wavelength of the reflected signal, correlating the modulation frequency and the instantaneous wavelength with a sensing location, and estimating a value of the parameter at the sensing location based on at least the instantaneous wavelength.

2. The method of claim 1, wherein the optical source is configured as part of an incoherent reflectometry system, and the control signal is configured to chaotically vary the output by introducing noise to an input of the optical source, the noise configured to reduce effects of coherence noise experienced during incoherent reflectometry operations.

3. The method of claim 1, wherein the optical source is an electrically driven optical source excited by a drive current, and transmitting the control signal includes applying the control signal to the drive current to chaotically vary the drive current.

4. The method of claim 1, further comprising combining the reflected signal with a reference signal to generate a combined signal indicative of the parameter.

5. The method of claim 1, wherein chaotically varying the wavelength includes chaotically changing the wavelength over time within a selected linewidth that includes the central wavelength.

6. The method of claim 4, further comprising transforming the combined signal from a frequency domain into a time domain to provide a measurement set corresponding to each selected length of the optical fiber.

7. The method of claim 1, wherein the control signal chaotically varies the output via at least one of a random number generator, a pseudo-random number generators and a noise generator.

8. A system for estimating a parameter, the system comprising:

a coherent optical source in optical communication with an optical fiber, the optical source configured to generate an optical signal having a central wavelength, the optical fiber configured to receive the optical signal and including a plurality of sensing locations disposed along the optical fiber and configured to reflect light;

a modulator configured to modulate the optical signal via an oscillating modulation signal having a time-varying modulation frequency;

a controller in communication with the optical source, the controller configured to transmit a control signal to the optical source, the control signal configured to chaotically vary a wavelength of the optical source and generate a chaotically excited optical signal, wherein chaotically varying the wavelength introduces noise and decreases the coherence of the optical signal, and chaotically varying the wavelength includes periodically applying a random wavelength change relative to the central wavelength, each wavelength change correlated with a different sensing location;

a detector configured to receive a reflected signal including light reflected from the at least one sensing location; and a processor configured to determine the modulation frequency and an instantaneous wavelength of the reflected signal, correlate the modulation frequency and the instantaneous wavelength with a sensing location, and estimate a value of the parameter at the sensing location based on at least the instantaneous wavelength.

9. The system of claim 8, wherein the optical source is configured as part of an incoherent reflectometry system, and the control signal is configured to chaotically vary the output by introducing noise to an input of the optical source, the noise configured to reduce effects of coherence noise experienced during incoherent reflectometry operations.

10. The system of claim 8, wherein the optical source is an electrically driven optical source excited by a drive current, and the controller is configured to transmit the control signal by applying the control signal to the drive current to chaotically vary the drive current.

11. The system of claim 8, wherein the processor configured to combine the reflected signal with a reference signal to generate a combined signal indicative of the parameter.

12. The system of claim 8, wherein the control signal chaotically varies the wavelength by chaotically changing the wavelength over time within a selected linewidth that includes the central wavelength.

13. The system of claim 11, wherein the processor is configured to transform the combined signal from a frequency domain into a time domain to provide a measurement set corresponding to each selected length of the optical fiber.

14. The system of claim 8, wherein the control signal chaotically varies the output via at least one of a random number generator, a pseudorandom number generators and a noise generator.

\* \* \* \* \*